United States Patent

Nedelec et al.

[11] 4,218,375
[45] Aug. 19, 1980

[54] 4H-THIENO-[3,2-B][1]-BENZAZEPINES

[75] Inventors: Lucien Nedelec, Le Raincy; Jacques Guillaume, Aulnay-sous-Bois; Claude Dumont, Nogent-sur-Marne, all of France

[73] Assignee: Roussel Uclaf, Paris, France

[21] Appl. No.: 701,152

[22] Filed: Jun. 30, 1976

[30] Foreign Application Priority Data

Jul. 10, 1976 [FR] France ................ 75 21649

[51] Int. Cl.$^2$ ............................ C07D 513/02
[52] U.S. Cl. ................... 260/330.3; 424/250
[58] Field of Search ............ 260/332.3 P; 549/43

[56] References Cited

U.S. PATENT DOCUMENTS

| 3,267,094 | 8/1966 | Drukker et al. | 260/268 TR |
| 3,637,660 | 1/1972 | Eriksoo et al. | 260/332.3 P X |
| 3,787,445 | 1/1974 | Nedelec et al. | 260/332.3 P X |
| 3,856,910 | 12/1974 | Nedelec et al. | 260/332.3 P X |

Primary Examiner—Glennon H. Hollrah
Assistant Examiner—D. B. Springer
Attorney, Agent, or Firm—Hammond & Littell, Weissenberger and Muserlian

[57] ABSTRACT

Novel 4H-thieno-[3,2-b][1]-benzazepines of the formula

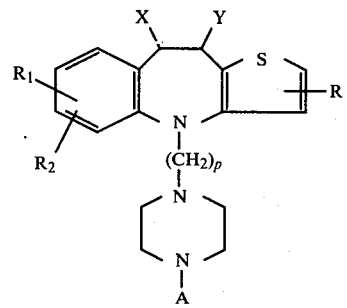

wherein R, $R_1$ and $R_2$ are individually selected from the group consisting of hydrogen and halogen, X and Y are hydrogen or together form a carbon-carbon double bond, p is 2 or 3 and A is selected from the group consisting of alkyl of 1 to 5 carbon atoms and hydroxyalkyl of 2 to 5 carbon atoms and their non-toxic, pharmaceutically acceptable acid addition salts having neuro sedative and antihistaminic properties and their preparation and intermediates therefor.

2 Claims, No Drawings

4H-THIENO-[3,2-b][1]-BENZAZEPINES

STATE OF THE ART

U.S. Pat. Nos. 3,787,445 and 3,856,910 described thieno benzazepines useful as anti-depressants but they do not contain a substituted piperazino group.

OBJECTS OF THE INVENTION

It is an object of the invention to provide the novel compounds of formula I and their non-toxic, pharmaceutically acceptable acid addition salts.

It is another object of the invention to provide a novel process for the preparation of the compounds of formula I as well as novel intermediates therefor.

It is an additional object of the invention to provide novel neuro-sedative and anti-histaminic compositions as well as a novel method of treating anxiety in warm-blooded animals.

These and other objects and advantages of the invention will become obvious from the following detailed description.

THE INVENTION

The novel compounds of the invention are selected from the group consisting of 4H-thieno-[3,2-b][1]-benzazepines of the formula

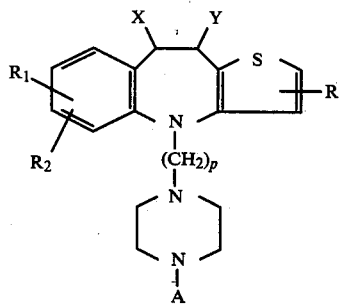

wherein R, $R_1$ and $R_2$ are individually selected from the group consisting of hydrogen and halogen, X and Y are hydrogen or together form a carbon-carbon double bond, p is 2 or 3 and A is selected from the group consisting of alkyl of 1 to 5 carbon atoms and hydroxyalkyl of 2 to 5 carbon atoms and their non-toxic, pharmaceutically acceptable acid addition salts.

Examples of R, $R_1$ and $R_2$ are hydrogen and halogens such as chlorine, fluorine or bromine. Examples of alkyl of 1 to 5 carbon atoms are methyl, ethyl, propyl, butyl, sec.-butyl and tert.-butyl and of hydroxy alkyl of 2 to 5 carbon atoms are hydroxyethyl, hydroxypropyl and hydroxybutyl.

Examples of suitable acids to form the non-toxic, pharmaceutically acceptable acid addition salts are inorganic acids such as hydrochloric acid, hydrobromic acid, hydroiodic acid, nitric acid, sulfuric acid or phosphoric acid and organic acids such as formic acid, acetic acid, benzoic acid, maleic acid, fumaric acid, succinic acid, tartaric acid, citric acid, oxalic acid, glyoxylic acid, aspartic acid, alkane sulfonic acids such as methane sulfonic acid and aryl sulfonic acids such as benzene sulfonic acid.

Among the preferred compounds of formula I are those where p is 3 and most preferably when p is 3, and A is hydroxyalkyl of 2 to 5 carbon atoms and their acid addition salts. Specific preferred compounds are 4-[3-{4-(2-hydroxyethyl)-piperazin-1-yl}-propyl]-9,10-dihydro-4H-thieno-[3,2-b][1]-benzazepine and 4-[3-{4-(2-hydroxyethyl)-piperazin-1-yl}-propyl]-4H-thieno-[3,2-b][1]-benzazepine and their non-toxic, pharmaceutically acceptable acid addition salts.

The novel process of the invention for the preparation of the compounds of formula I comprises reacting a compound of the formula

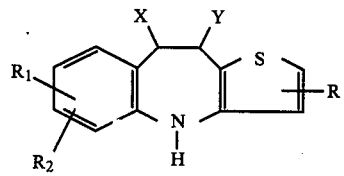

wherein R, $R_1$, $R_2$, X and Y have the above definitions with a 2-($\omega$-chloro-n-alkoxyl)-tetrahydropyran of the formula

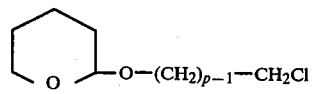

wherein p has the above definition at reflux in an organic solvent in the presence of an alkali metal hydride to obtain a compound of the formula

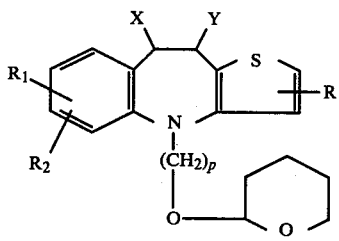

subjecting the latter to acid hydrolysis in an organic solvent to obtain a compound of the formula

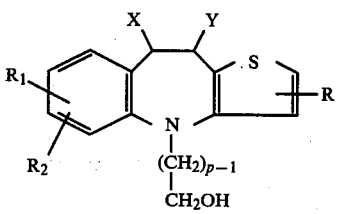

reacting the latter with an alkyl or an aryl sulfonic acid chloride of the formula

wherein B is lower alkyl or monocyclic aryl to obtain a compound of the formula

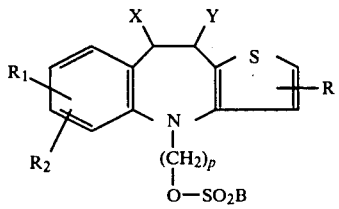

VI and reacting the latter with a piperazine of the formula

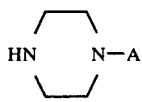

VII to obtain the corresponding compound of formula I which may be salified if desired.

In a preferred embodiment of the process, the reaction of the compounds of formulae II and III is effected in an aromatic solvent such as benzene, xylene or toluene in the presence of sodium hydride or potassium hydride. The acid hydrolysis is effected with a mineral acid such as hydrochloric acid, sulfuric acid or perchloric acid or an alkyl or aryl sulfonic acid such as methane sulfonic acid, benzene sulfonic acid or p-toluene sulfonic acid and the solvent is preferably an alkanol such as methanol, ethanol or propanol. The sulfonic acid chloride is preferably the chloride of methane sulfonic acid, benzene sulfonic acid or p-toluene sulfonic acid.

The most preferred process of the invention comprises reacting compounds II and III at reflux in xylene in the presence of sodium hydride, subjecting the resulting product to hydrolysis with hydrochloric acid in ethanol and reacting the resulting product with tosyl chloride.

The acid addition salts of formula I may be prepared by reacting substantially stoichiometric amounts of a mineral or organic acid with a product of formula I with or without isolation of the free base.

The novel neuro-sedative and anti-histaminic compositions of the invention are comprised of at least one compound of formula I and its non-toxic, pharmaceutically acceptable acid addition salts and an inert pharmaceutical carrier. The compositions may be in the form of tablets, dragees, gelules, granules, suppositories or injectable solutions or suspensions prepared in the usual manner.

Examples of suitable excipients or inert pharmaceutical carriers are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispensants and emulsifiers.

The compositions are useful for the treatment of anxiety, irritability, hyperemotivity or uneasiness. Particularly suitable are the compounds of formula I wherein p is 3 and also where p is 3 and A is hydroxyalkyl of 2 to 5 carbon atoms and their acid addition salts.

The novel method of the invention for treating anxiety in warm-blooded animals including humans comprises administering to warm-blooded animals an effective amount of at least one compound of formula I and its non-toxic, pharmaceutically acceptable acid addition salts. The compounds may be administered orally, rectally or parenterally and the usual useful dosage is 0.5 to 5 mg/kg depending upon the compound and the method of the administration.

The novel intermediates of the invention have the formula

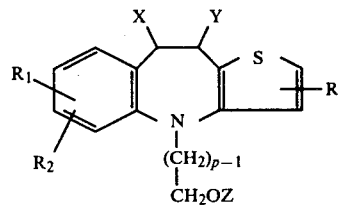

VIII wherein R, $R_1$, $R_2$, X, Y and p have the above definition and Z is selected from the group consisting of 2-tetrahydropyran, hydrogen and —$SO_2B$ wherein B has the above definition.

Among the compounds of formula VIII are 4-[3-(2-tetrahydropyranyloxy)-propyl]-9,10-dihydro-4H-thieno-[3,2-b][1]-benzazepine, 4-[3-(2-tetrahydropyranyloxy)-propyl]-4H-thieno-[3,2-b][1]-benzazepine, 4-(3-hydroxypropyl)-9,10-dihydro-4H-thieno-[3,2-b][1]-benzazepine, 4-(3-hydroxypropyl)-4H-thieno-[3,2-b][1]-benzazepine, 4-[3-(4-p-toluene sulfonyloxy)-propyl]-9,10-dihydro-4H-thieno-[3,2-b][1]-benzazepine and 4-[3-(4-p-toluene sulfonyloxy)-propyl]-4H-thieno-[3,2-b][1]-benzazepine.

The compounds of formula III may be prepared by the process described in J.A.C.S., Vol. 70 (1948), p 4187 for the preparation of 2-(3-chloropropoxy)-tetrahydropyran by reacting dihydropyran with Cl—$(CH_2)_{p-1}$—$CH_2OH$ where p has the above definition.

In the following examples there are described several preferred embodiments to illustrate the invention. However, it should be understood that the invention is not intended to be limited to the specific embodiments.

EXAMPLE 1

4-[3-{4-(2-hydroxyethyl)-piperazin-1-yl}-propyl]-4H-thieno-[3,2-b][1]-benzazepine and its dihydrochloride STEP A: 4-(3-hydroxypropyl)-4H-thieno-[3,2-b][1]-benzazepine A mixture of 4 g of 4H-thieno-[3,2-b][1]-benzazepine, 80 ml of xylene and 2.4 g of sodium hydride as a 50% suspension in oil was stirred under nitrogen and was then refluxed for an hour. Then, 12 ml of 2-(3-chloropropoxy)-tetrahydropyran were added thereto and the mixture was refluxed for 3 more hours and was then cooled. The mixture was poured into 400 g of ice and was extracted with ethyl acetate. The organic extracts were washed with water, dried over magnesium sulfate and were evaporated to dryness under reduced pressure. The residue was dissolved in 80 ml of ethanol and 4 ml of 6 N hydrochloric acid were added to the solution. After 4 hours at room temperature, the mixture was poured over 400 g of ice and the aqueous phase was decanted and extracted with methylene chloride. The organic extracts were washed with water, dried over magnesium sulfate and were evaporated to dryness under reduced pressure. The residue was chromatographed over silica gel and was eluted with a 7-3 benzene-ethyl acetate mixture to obtain 4.2 g of 4-(3-hydroxypropyl)-4H-thieno-[3,2-b][1]-benzazepine in the form of an oil.

STEP B: 4-[3-(4-p-toluene sulfonyloxy)-propyl]-4H-thieno-[3,2-b][1]-benzazepine 7 g of tosyl chloride were added to a solution of 7 g of 4-(3-hydroxypropyl)-4H-thieno-[3,2-b][1]-benzazepine in 35 ml of pyridine and the mixture was stirred under an inert gas for an hour. The mixture was poured into 200 ml of ice and water and the mixture was extracted with ethyl acetate. The ethyl acetate extracts were successively washed with water, a saturated sodium bicarbonate solution, water, 2 N hydrochloric acid and finally water. The extracts were dried over magnesium sulfate and evaporated to dryness under reduced pressure to obtain 5.4 g of 4-[3-(4-p-toluene sulfonyloxy)-propyl]-4H-thieno-[3,2-b][1]-benzazepine melting at 80° C.

Analysis: $C_{22}H_{21}O_3NS_2$: Calculated: %C, 64.21; %H, 5.14; %N, 3.40; %S, 15.58. Found: %C, 64.4; %H, 5.4; %N, 3.3; %S, 15.4.

STEP C: 4-[3-{4-(2-hydroxyethyl)-piperazin-1-yl}-propyl]-4H-thieno-[3,2-b][1]-benzazepine and its dihydrochloride A solution of 4 g of p-toluene sulfonate of 4-(3-hydroxypropyl)-4H-thieno-[3,2-b][1]-benzazepine in 20 ml of toluene was formed under an inert gas and then 4 ml of N-(2-hydroxyethyl)-piperazine were added dropwise. The mixture was refluxed for one hour and was then cooled and diluted with water and extract with ethyl acetate. 2 N hydrochloric acid was added and the extracts were made alkaline with sodium hydroxide. The mixture was extracted with methylene chloride and the organic phase was washed with water, dried over magnesium sulfate and evaporated to dryness under reduced pressure to obtain 3.8 g of 4-[3-{4-(2-hydroxyethyl)-piperazin-1-yl}-propyl]-4H-thieno-[3,2-b][1]-benzazepine in the form of a yellow oil.

3 g of the latter product were dissolved in 10 ml of ethanol and 1.5 ml of an ethanol solution saturated with hydrochloric acid were added dropwise with stirring to the solution. Crystallization was induced and the crystals were recovered by filtration, were washed with ethanol and dried to obtain 2.65 g of the dihydrochloride of the said benzazepine melting at 214°–215° C.

Analysis: $C_{21}H_{29}Cl_2N_3OS$: Calculated: %C, 57.01; %H, 6.60; %N, 9.49; %S, 7.24; %Cl, 16.02. Found: %C, 57; %H, 6.6; %N, 9.3; %S, 7.5; %Cl, 15.7.

EXAMPLE 2

4-[3-{4-(2-hydroxyethyl)-piperazin-1-yl}-propyl]-9,10-dihydro-4H-thieno-[3,2-b][1]-benzazepine and its dihydrochloride STEP A: 4-(3-hydroxypropyl)-9,10-dihydro-4H-thieno-[3,2-b][1]-benzazepine A mixture of 6 g of 9,10-dihydro-4H-thieno-[3,2-b][1]-benzazepine and 120 ml of xylene was heated to reflux and 3.6 g of sodium hydride in a 50% suspension in oil were added thereto dropwise. The mixture was refluxed with stirring for an hour and then 18 ml of 2-(3-chloropropoxy)-tetrahydropyran were added dropwise over 5 minutes. The mixture was refluxed another 3 hours and was cooled and poured into 300 ml of ice and water. The aqueous phase was decanted and was extracted with ethyl acetate. The organic extracts were washed with water, dried over magnesium sulfate and evaporated to dryness under reduced pressure. The residue was dissolved in 120 ml of ethanol and 6 ml of 6 N hydrochloric acid were added dropwise. The mixture was stirred for 3 hours at room temperature and was then poured into 600 ml of ice and water. The mixture was extracted with methylene chloride and the organic extracts were washed with water, dried over magnesium sulfate and evaporated to dryness under reduced pressure. The residue was chromatographed over silica gel and was eluted with a 7-3 benzene-ethyl acetate to obtain 7 g of 4-(3-hydroxypropyl)-9,10-dihydro-4H-thieno-[3,2-b][1]-benzazepine melting at 73° C.

Analysis: $C_{15}H_{17}NOS$: Calculated: %C, 69.46; %H, 6.61; %N, 5.40; %S, 12.36. Found: %C, 69.2; %H, 6.7; %N, 5.3; %S, 12.1.

STEP B: 4-[3-(4-p-toluene sulfonyloxy)-propyl]-9,10-dihydro-4H-thieno-[3,2-b][1]-benzazepine 6.7 g of tosyl chloride were added to a solution of 6.7 g of the product of Step A in 35 ml of pyridine and the mixture was stirred at room temperature for 1½ hours and was then poured into 150 ml of ice and water. The mixture was extracted with ethyl acetate and the extracts were successively washed with water, 2 N hydrochloric acid, water, sodium bicarbonate solution and then water. The extracts were dried and evaporated to dryness under reduced pressure. The residue was crystallized from isopropyl ether to obtain 6.73 g of 4-[3-(4-p-toluene sulfonyloxy)-propyl]-9,10-dihydro-4H-thieno-[3,2-b][1]-benzazepine melting at 92° C.

Analysis: $C_{22}H_{23}NO_3S_2$: Calculated: %C, 63.89; %H, 5.60; %N, 3.39; %S, 15.61. Found: %C, 63.8; %H, 5.3; %N, 3.3; %S, 15.6.

STEP C: 4-[3-{4-(2-hydroxyethyl)-piperazin-1-yl}-propyl]-9,10-dihydro-4H-thieno-[3,2-b][1]-benzazepine and its dihydrochloride 6 ml of N-(2-hydroxyethyl)-piperazine were added dropwise to a solution of 6 g of the product of Step B in 30 ml of toluene and the mixture was refluxed for 1½ hours and was then cooled. The mixture was diluted with water and was extracted with ethyl acetate. The organic extracts were washed with water and was extracted with 2 N hydrochloric acid. The mixture was alkanized by addition of sodium hydroxide and was extracted with methylene chloride. The organic extracts were washed with water, dried and evaporated to dryness under reduced pressure. The residue was chromatographed over silica gel and was eluted with a 6-3-1 chloroform-acetone-triethylamine mixture to obtain 4.53 g of 4-[3-{4-(2-hydroxyethyl)-piperazin-1-yl}-propyl]-9,10-dihydro-4H-thieno-[3,2-b][1]-benzazepine.

The latter product was dissolved in 18 ml of ethanol and an ethanol solution saturated with hydrochloric acid was added dropwise until the pH was 1. The mixture was cooled and vacuum filtered. The recovered crystals were washed with ethanol and dried under reduced pressure. The product was crystallized from a methanol-ethanol mixture to obtain 4.12 g of the dihydrochloride of the said benzazepine melting at 246°–248° C.

Analysis: $C_{21}H_{31}Cl_2N_3OS$: Calculated: %C, 56.75; %H, 7.03; %N, 9.45; %Cl, 15.95; %S, 7.21. Found: %C, 56.4; %H, 7.1; %N, 9.2; %Cl, 16.1; %S, 7.2.

EXAMPLE 3

Tablets were prepared with 50 mg of 4-[3-{4-(2-hydroxyethyl)-piperazin-1-yl}-propyl]-9,10-dihydro-4H-thieno-[3,2-b][1]-benzazepine dihydrochloride or 50 mg of 4-[3-{4-(2-hydroxyethyl)-piperazin-1-yl}-propyl]-4H-thieno-[3,2-b][1]-benzazepine dihydrochloride and or excipient of lactose, starch, talc and magnesium stearate.

PHARMACOLOGICAL DATA

A. Chimney Test

This test consisted of placing a mouse in the end of a glass tube 30 cm long with a diameter adapted to the height of the mouse. When the tube was straightened vertically in a rapid motion, the animal, with its head at the base, returned normally in the length of the tube in an average of 30 seconds. The test was run 30 minutes after the intraperitoneal administration of the test product and the $DE_{50}$ dose, that dose which prevents 50% of the animals from effecting the raising in less than 30 seconds was determined.

B. Antagonism to toxicity of amphetaminic compounds

The antagonism to the toxicity of amphetaminic group was determined on groups of 10 male mice in a crystallizer with a diameter of 20 cm and a height of 9 cm covered with a grill. The animals received a intraperitoneal injection of 15 mg/kg of dexamphetamine sulfate 30 minutes after the oral administration of the test product. The mortality for each group was totaled 24 hours after the dexamphetamine sulfate injection and the $DE_{50}$ dose, the dose which reduced the mortality by 50%, was determined.

C. Antagonism to vomiting caused by apomorphine

The antagonism to vomiting provoked by apomorphine was studied on dogs by the technique of Chen et al [J. Pharmac. exp. Therap., Vol. 93 (1950), p 245-250] wherein the test compound was subcutaneously injected 30 minutes before subcutaneous injection of 0.1 mg/kg of apomorhine hydrochloride. The number of vomits was observed over 30 minutes after the apomorphine injection and for each dose studied, the tests were crossed at 8 day intervals for lots of 2 dogs. The $DE_{50}$ dose or the dose that reduced the number of vomits by 50% was determined.

D. Antagonism to histamine toxicity

This test was determined on guinea pigs and the test product was subcutaneously administered 30 minutes before intraveinous administration of 0.8 mg/kg of histamine hydrochloride. The number of deaths after 10 minutes of the last injections was noted and the $DE_{50}$ or the dose which reduced the mortality of the animals by 50% was determined.

E. Acute Toxicity

The $DL_{50}$ on the dose which killed 50% of the animals was determined by intraperitoneal administration of the test compounds to mice. The mortality was determined 48 hours after the injection. The results of Tests A to E are reported in Table I.

TABLE I

| Dihydrochloride of product of Example | $DE_{50}$ in mg/kg - Test | | | | $DL_{50}$ in mg/kg Test E |
|---|---|---|---|---|---|
| | A | B | C | D | |
| 1 | 50 | 50 | 2.5 | 0.3 | 150 |
| 2 | 28 | 10 | 0.4 | 0.2 | 150 |

Various modification of the products and method of the invention may be made without departing from the spirit or scope thereof and it is to be understood that the invention is to be limited only as defined in the appended claims.

We claim:

1. A compound of the formula

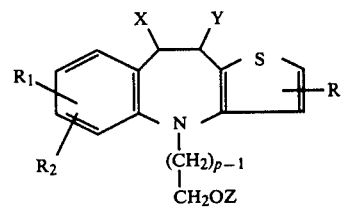

wherein R, $R_1$ and $R_2$ are individually selected from the group consisting of halogen and hydrogen, X and Y are hydrogen or together form a carbon-carbon double bond, p is 2 or 3 and Z is selected from the group consisting of 2-tetrahydropyran, hydrogen and -$SO_2B$ wherein B is lower alkyl or monocyclic aryl.

2. A compound of claim 1 selected from the group consisting of 4-[3-(2-tetrahydropyranyloxy)-propyl]-9,10-dihydro-4H-thieno-[3,2-b][1]-benzazepine, 4-[3-(2-tetrahydropyranyloxy)-propyl]-4H-thieno-[3,2-b][1]-benzazepine, 4-(3-hydroxypropyl)-9,10-dihydro-4H-thieno-[3,2-b][1]-benzazepine, 4-(3-hydroxypropyl)-4H-thieno-[3,2-b][1]-benzazepine, 4-[3-(4-p-toluene sulfonyloxy)-propyl]-9,10-dihydro-4H-thieno-[3,2-b][1]-benzazepine and 4-[3-(4-p-toluene sulfonyloxy)-propyl]-4H-thieno-[3,2-b][1]-benzazepine.

* * * * *